United States Patent
Zhu et al.

(10) Patent No.: US 6,670,520 B2
(45) Date of Patent: Dec. 30, 2003

(54) REDUCTIVE AMINATION FOR ALDEHYDE NEUTRALIZATION

(75) Inventors: Peter Zhu, Irvine, CA (US); Xiaolan Chen, Irvine, CA (US); Charles G. Roberts, Long Beach, CA (US)

(73) Assignee: Ethicon, Inc., Somerville, NJ (US)

( * ) Notice: Subject to any disclaimer, the term of this patent is extended or adjusted under 35 U.S.C. 154(b) by 231 days.

(21) Appl. No.: 09/747,230

(22) Filed: Dec. 22, 2000

(65) Prior Publication Data

US 2001/0025110 A1 Sep. 27, 2001

Related U.S. Application Data

(63) Continuation-in-part of application No. 09/321,964, filed on May 28, 1999, now Pat. No. 6,399,850.

(51) Int. Cl.$^7$ ................................................ A62D 3/00
(52) U.S. Cl. ........................ 588/205; 210/749; 210/908
(58) Field of Search ........................ 588/205; 210/749, 210/908

(56) References Cited

U.S. PATENT DOCUMENTS

| | | | |
|---|---|---|---|
| 3,892,523 A | | 7/1975 | Reclich et al. |
| 4,786,287 A | * | 11/1988 | Nashef et al. ................. 600/36 |
| 5,157,123 A | * | 10/1992 | Zara et al. .................... 436/547 |
| 5,352,368 A | * | 10/1994 | Honeycutt ................... 210/749 |
| 5,567,685 A | | 10/1996 | Linden et al. |
| 5,919,472 A | * | 7/1999 | Trescony et al. ............ 424/400 |
| 6,043,405 A | * | 3/2000 | Honeycutt et al. .......... 210/633 |
| 6,153,748 A | | 11/2000 | Fuchs et al. |
| 2002/0117449 A1 | * | 8/2002 | Zhu et al. .................... 210/679 |

FOREIGN PATENT DOCUMENTS

| | | | |
|---|---|---|---|
| DE | 197 04 615 a1 | | 8/1998 |
| JP | 04002350 A | * | 1/1992 ............. A61L/9/01 |
| JP | 7204661 | | 8/1995 |

OTHER PUBLICATIONS

Kem Medical Products Corp., Advanced Sterilizaion Products, Dec. 2000, Kem Medical Products, All pages.*
John McMurray, Organic Chemistry, 1992, no month, Brooks/Cole, 3rd Ed., pp. 635, 636, 823, 976.*
Non-confidential correspondence and literature from KEM Medical Products Corp.—Dated Feb. 28, 2001 ; Product Brochures (Glut–RX™ Glutaraldehyde Solution Neutralizer, KemSure™ OPA Solution Neutralizer, Neutralizing Spill Control Kits for glutaraldehyde, Neutralizing Absorbent Mats for Glutararaldehyde, Neutralizing Absorbent Mats of OPA, Neutralizing Spill Control Kits of OPA, Safety Nozzles); Results of Toxicity Test conducted From Nov. 29 Through Dec. 3, 2000 With a Neutralized Cidex™ OPA Solution, Jan. 2001 ; Results of Toxicity Test Using Neutralized Cidex™ Solution Conducted from Oct. 18 Through 22, 2000 Dec. 2000.
English Translation of Patent Application Disclosure (Kokai) No.: H–204661, Application No: H6–4417; Filing Date; Jan. 20, 1994 (Japanese patent submitted in previous Information Disclosure Statement submitted on Apr. 2, 2001).
H. Y. Cheung, M. R. Brown, "Evaluation of glycine as an inactivator of glutaraldehyde," 34 J. Pharm. 211 (1982) No month.
Japanese Abstract (English Equivalent of Patent No: JP 407204661A (Application No. JP06004416), "Treatment Agent of Waste Glutaraldehyde Liquid and Treatment of Waste", Aug. 8, 1995.
Seyhan N. Ege, "Organic Chemistry, Structure and Reactivity", Third Edition, 1994m o, 534–535 No month.
Non-confidential correspondence and literature from KEM Medical Products Corp.–Dated Feb. 28, 2001 ; Product Brochures (Glut–RX™ Glutaraldehyde Solution Neutralizer, KemSure™ OPA Solution Neutralizer, Neutralizing Spill Control Kits for glutaraldehyde, Neutralizing Absorbent Mats for Glutararaldehyde, Neutralizing Absorbent Mats of OPA, Neutralizing Spill Control Kits of OPA, Neutralizing Spill Control Kits of OPA, Safety Nozzles) ; Results of Toxicity Test conducted From Nov. 29 Through Dec. 3, 2000 With a Neutralized Cidex™ OPA Solution, Jan. 2001 ; Results of Toxicity Test Using Neutralized Cidex™ Solution Conducted from Oct. 18 Through 22, 2000 Dec. 2000.
English Translation of Paten Application Disclosure (Kokai) Number: H–204661, Application Number: H6–4417; Filing Date: Jan. 20, 1994 (Japanese patent submitted in previous Information Disclosure Statement submitted on Apr. 2, 2001.

* cited by examiner

*Primary Examiner*—Steven Bos
*Assistant Examiner*—Anthony J Kuhar

(57) ABSTRACT

Methods, compositions, and devices for alleviating the problems of toxic discharge of aldehydes present in waste streams are disclosed. The methods relate to reducing neutralized aldehydes wherein the neutralized aldehydes are formed by treating aldehydes with amino acids and thereinafter are reduced. These reduced, neutralized aldehydes do not revert back to toxic aldehydes, but form amino acids and thus allow waste containing aldehyde to be more environmentally safely disposed.

21 Claims, 4 Drawing Sheets

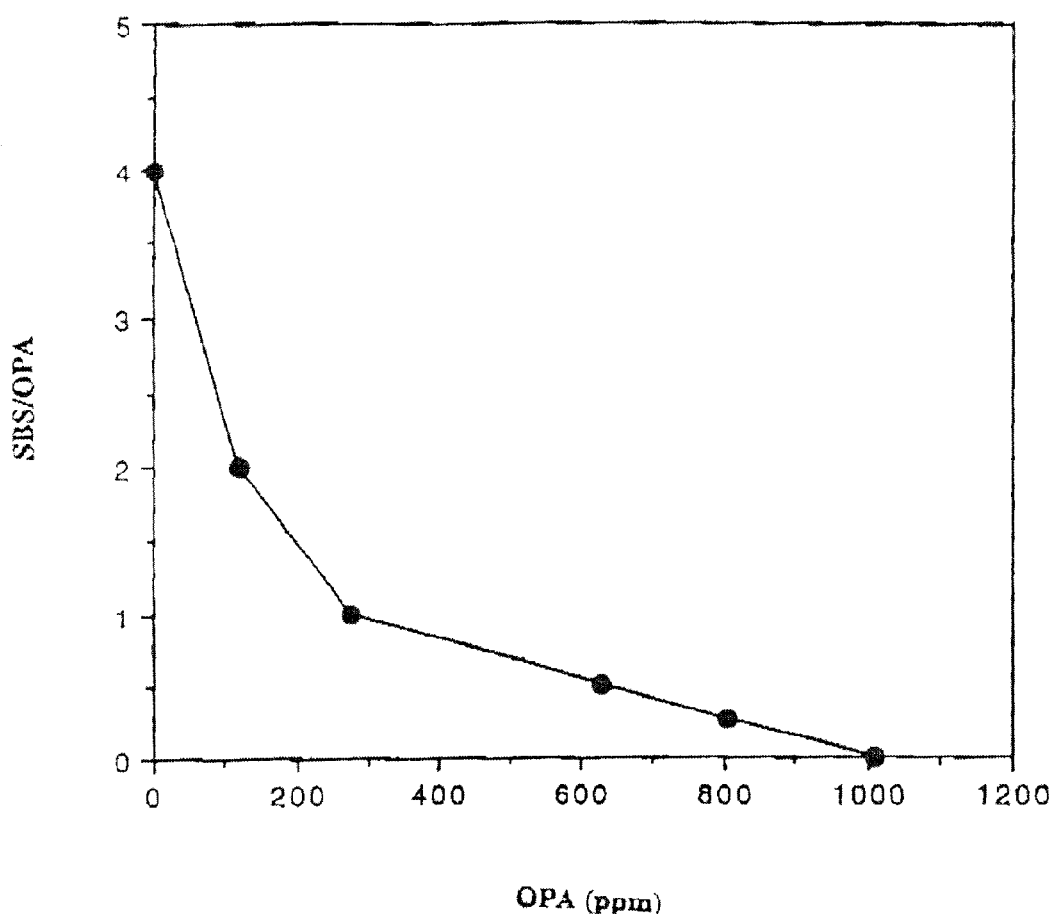
Figure 1: Ratio of SBS:OPA vs. Concentration OPA Remaining After 30 Minutes From Combining The Ingredients.

Amino acid and reducing agent (Pre-mixed or separated)
are added at the same time Amino acid is added
before
the reducing agent

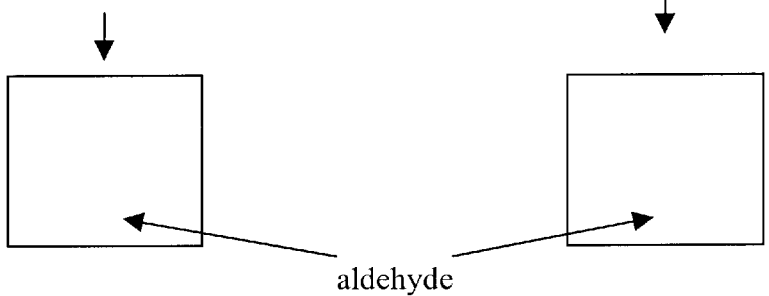

aldehyde

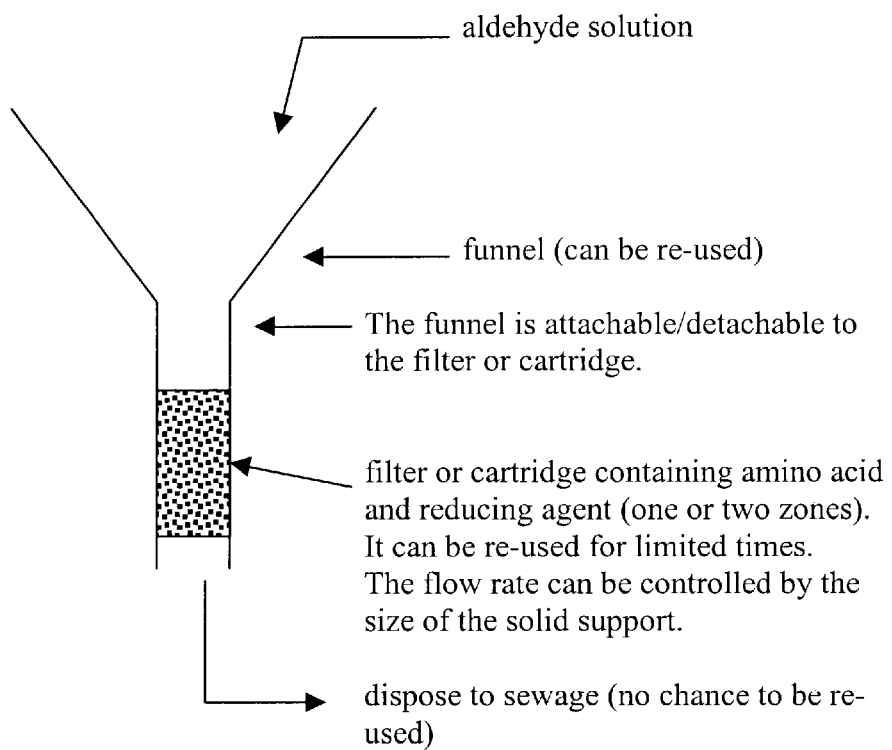

aldehyde solution funnel (can be re-used)

The funnel is attachable/detachable to the filter or cartridge.

filter or cartridge containing amino acid and reducing agent (one or two zones). It can be re-used for limited times. The flow rate can be controlled by the size of the solid support.

dispose to sewage (no chance to be re-used)

FIG. 3a

REDUCTIVE AMINATION FOR ALDEHYDE NEUTRALIZATION

RELATED APPLICATIONS

This patent application is a continuation-in-part of co-pending and commonly assigned patent application U.S. Ser. No. 09/321,964, filed May 28, 1999 entitled "Aldehyde Neutralizer", now U.S. Pat. No. 6,399,850, the disclosure of which is incorporated by reference.

BACKGROUND OF THE INVENTION

1. Field of the Invention

The invention relates to neutralization of aldehydes for the purpose of complying with waste disposal requirements established by federal and state environmental protection agencies, in particular, with forming non-reversible neutralized aldehydes which do not revert back to toxic aldehydes.

2. Description of Related Art

Waste disposal of aldehydes has become increasingly more difficult over the years. Treatment of wastes containing a certain amount of aldehyde prior to placement of the waste into the environment is required by law. The extent of such treatment may vary depending upon the location of where the waste is generated and the stringency of the environmental standards in that area. For example, waste containing aldehyde may be classified as a hazardous waste in California under 22 CAL. CODE REGS., TIT. 22, §66696. Formaldehyde also may be considered a hazardous waste on the federal level under 40 C.F.R. §261.33(e) if it is a commercial chemical product (e.g., pure technical grade formaldehyde or formaldehyde is the sole active ingredient of the product that is to be disposed). Every state has an environmental regulation that is at least as stringent as this formaldehyde standard. State regulations also may be more stringent than this standard.

Additionally, facilities that discharge waste water to Publicly Owned Treatment Works ("POTW") or directly into navigable waters may be required to meet standards that are established by a government agency. The standard may vary for each facility depending upon the quality of the receiving water and the concentration of aldehyde found in the waste water that is discharged into the environment by industry in that area.

Waste containing aldehyde may be generated by a variety of processes. For example, aldehydes such as glutaraldehyde and ortho-phthalaldehyde ("OPA") are used in disinfecting medical devices or instruments. Waste containing aldehydes also may be generated by painting operations, stripping operations related to floors, or other manufacturing operations.

Typically, ammonia and sodium bisulfite ("SBS") are used to treat many aldehydes. These compounds, however, have not proven to be effective at neutralizing OPA in accordance with environmental regulations.

A waste is classified as a hazardous waste in California if the waste being examined "has an acute aquatic 96-hour $LC_{50}$ less than 500 milligrams per liter (mg/L) when measured in soft water (total hardness 40 to 48 milligrams per liter of calcium carbonate) with fathead minnows . . . " 22 CAL. CODE REGS., TIT. 22, §66696. $LC_{50}$ represents the concentration of a waste that is necessary to kill 50% of a particular animal exposed to a waste.

Note that a nonhazardous waste is generally considered by federal and state environmental agencies as a waste that does not satisfy the criteria set forth in defining a hazardous waste. Therefore, wastes generated in California that have a $LC_{50}>500$ mg/L are nonhazardous wastes and wastes having $LC_{50}<500$ mg/L are classified as hazardous. SBS, for example, in combination with OPA, produces a product that is generally considered hazardous under California environmental law as shown in Table 1 by $LC_{50}$ being consistently below 500 mg/L. For this study, CIDEX®OPA (commercially available from Advanced Sterilization Products®, a Johnson & Johnson Company of Irvine, Calif.) was used to supply the OPA.

TABLE 1

Neutralization Of OPA Using SBS

| Sample Type | OPA Content (%) | $LC_{50}$ (mg/L) | Comments |
| --- | --- | --- | --- |
| Fresh CIDEX ® OPA at 0.3% OPA | 0.301% | 31.1 mg/L | 1 |
| Fresh CIDEX ® OPA at 0.15% OPA | 0.158% | 50.4 mg/L | 2 |
| Reuse CIDEX ® OPA at 0.3% OPA | 0.295% | 31.1 mg/L | 3 |
| SBS/OPA = 4:1 | N/A | 68.3 mg/L | 4 |
| SBS/OPA = 2:1 | N/A | 46.3 mg/L | 5 |

1 Fresh CIDEX ® OPA at 0.3% OPA was prepared by diluting the fresh Cidex OPA solution with deionized water.
2. Fresh CIDEX ® OPA at 0.15% OPA was prepared by diluting the fresh Cidex OPA solution with deionized water to the level of 0.15% of OPA.
3. Reuse of CIDEX ® OPA at 0.3% OPA was prepared by diluting the simulated reuse CIDEX ® OPA (14 days) with deionized water.
4. SBS/OPA = 4:1, 10% SBS (10 ml) was combined with 100 ml of the fresh CIDEX ® OPA solution at 0.3% OPA (sample 1 above) at the SBS/OPA molar ratio of 4 to 1 for 30 minutes, and then the combined solution was used in the 22 CAL. CODE REGS., TIT. 22, § 66696 test for California.
5. SBS/OPA = 2:1, 10% SBS (5 ml) was combined with or 100 ml of the fresh CIDEX ® OPA solution at 0.3% OPA (sample 1 above) at the SBS/OPA molar ratio of 2 to 1 for 30 minutes, and then the combined solution was used for the fish test in the 22 CAL. CODE REGS., TIT. 22, § 66696 test for California In addition to lacking the ability to effectively neutralize OPA, ammonia and SBS are problematic since they may be harmful to the environment.

FIG. 1 shows that when OPA is combined with SBS at the molar ratio of SBS/OPA=4:0 for 30 minutes, OPA has been neutralized since the OPA concentration is nondetectable in a high performance liquid chromatography (HPLC) analysis method, which has detection limit for OPA at 10 ppm. However, the end product is still classified as a hazardous waste as shown in Table 1. Therefore, even though the aldehyde is neutralized completely by a neutralizer, the end product may still be a hazardous waste.

Although glycine has been shown to neutralize glutaraldehyde (see H. Y. Cheung & M. R. W. Brown, *Evaluation of Glycine As An Inactivator of Glutaraldehyde, ASP-934* J. Pharm. 211 (1982)), the toxicity of reaction products of glycine has not been studied. Therefore, it is not known from this article whether the reaction product is nonhazardous. Accordingly, it is desirable to have a neutralizer that effectively neutralizes aldehydes in compliance with environmental standards and is less toxic to the environment.

Furthermore, it has been observed that neutralization of aldehydes with amino acids under acidic conditions may reversibly form compounds called Schiff's bases. That is, once the Schiff's bases are formed under acidic conditions, the reverse reaction will occur to release back aldehydes. Another problem associated with amino acid neutralized aldehydes is that often the solution formed between the aldehyde and the amino acid has a dark color such as dark green or black. This occurs, for example, during the neutralization reaction between o-phthalaldehyde and the amino acid, glycine. Such color appearance has the perception that the resulting solution is not environmentally friendly even though the solution has been neutralized. Finally, not all methods relating to formation of neutralized aldehydes are as environmentally friendly as others are. This invention is intended to overcome the foregoing shortcomings relating to neutralization of aldehydes as hereinafter described.

SUMMARY OF THE INVENTION

Methods, compositions and devices are disclosed for neutralizing aldehydes to form a nonhazardous product which is non-reversible and environmentally friendly. In one aspect, the invention provides a generally nonhazardous means for neutralizing and reducing aldehydes to form environmentally friendly amino acids.

In one embodiment, the neutralization method comprises combining an amino acid in solution or in solid form with an aldehyde to form a neutralized aldehyde and then reducing the neutralized aldehyde to form an amino acid. Devices for neutralizing and reducing the aldehyde to an amino acid are also disclosed.

Among the advantages of the invention are: a more environmentally friendly end product as the reduced neutralized aldehydes are amino acids and are very similar in backbone structure to natural amino acids, and thus would be expected to be biodegradable and environmentally friendly; the prevention of possible reformation of the aldehydes from the Schiff's bases since the reduction of a Schiff's base is irreversible; the colors of the reduced neutralized aldehydes are pale, not dark or black which would reflect the appearance of a non-toxic material; and once reduced, there would be no further need to treat the waste and the waste could be immediately discharged.

Additional features, embodiments, and benefits will be evident in view of the figures and detailed description presented below.

BRIEF DESCRIPTION OF THE DRAWINGS

The features, aspects, and advantages of the invention will become more thoroughly apparent from the following detailed description, appended claims, and accompanying drawings in which:

FIG. 1 shows the ratio of SBS:OPA and the concentration of OPA remaining in solution after 30 minutes from combining the ingredients.

FIGS. 2a and 2b show schematic diagrams for mixing of amino acids and reducing agents with aldehydes.

FIGS. 3a, 3b, and 3c show schematic diagrams of devices embodying the principles of this invention.

DETAILED DESCRIPTION OF THE INVENTION

Figures 3B, 3C:
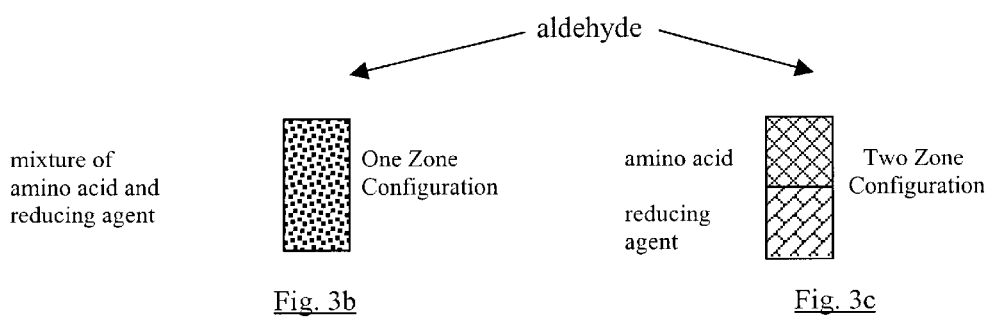

The invention relates to methods, compositions and devices particularly useful for the environmentally friendly and non-reversible neutralization of aldehydes present in waste generated from sterilizing medical devices (e.g., scalpels, scissors, endoscopes, etc.) or laboratory equipment (e.g., glassware) that have been exposed to microorganisms such as bacteria. As used herein, the term non-reversible is intended to refer to the substantial prevention of the neutralized aldehyde (e.g., amino acid treated aldehyde) from reverting back to the starting or unneutralized aldehyde.

Sterilizing includes disinfecting medical devices. The neutralizer comprises an amino acid selected from amino acids having polar R groups, amino acids having non-polar R groups and amino acids with charged R groups. In one embodiment, the chemical neutralizer is selected from one or more of alanine, proline, amino-caproic acid, phenylalanine, tryptophan, methionine, glycine, serine, cycteine, tyrosine, lysine, arginine, glutamine, aspartic acid, glutamic acid, and histidine.

To neutralize aldehydes, the neutralizer in solution or in solid form may be added to waste water that is in a tank (e.g., a neutralization tank at a waste water treatment plant), or in a small container (e.g., a bucket) where aldehydes must be neutralized before they are placed into a sewer system that may discharge to a POTW or into navigable waters. Solids contaminated with aldehydes (e.g., dirt, rags, or gloves, etc.) may be neutralized by directly adding the neutralizer to the solids or by placing the solids into a container with the neutralizer and, optionally, water.

Amino acids are an improvement over the typical chemicals such as ammonia or sodium bisulfite used to neutralize aldehydes since amino acids quickly and effectively neutralize aldehydes to a level prescribed by federal and state environmental agencies. Amino acids are also less expensive than products such as ammonia and sodium bisulfite.

There are a variety of amino acids that are useful in neutralizing aldehydes. These Amino acids include:

(1) Amino acids with apolar R groups (e.g., alanine, proline, amino-caproic acid, phenylalanine, tryptophan and methionine);
(2) Amino acids with polar R groups (e.g., glycine, serine, cysteine, tyrosine, and glutamine);
(3) Amino acids with charged R groups (e.g., aspartic acid, glutamic acid, lysine, arginine, and histidine); and,
(4) Peptides/polypeptides formed by any number or any type of amino acids and proteins.

A neutralized aldehyde product can be formed by reacting an amino group from an amino acid or proteins with an aldehyde group of aldehydes to produce N-substituted adducts (imines or Schiff's bases) as shown below.

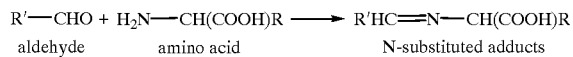

R'—CHO + H$_2$N—CH(COOH)R ⟶ R'HC=N—CH(COOH)R
aldehyde      amino acid      N-substituted adducts Table 2 shows the ratios of certain amino acids with a CIDEX® OPA solution and the time it takes the selected amino acids to neutralize OPA. CIDEX® OPA is used to disinfect medical devices. OPA is a dialdehyde. It is to be appreciated that the techniques described herein can be applied to most aldehydes present in a waste with the neutralization occurring, for example, according to the adduct formation described above for an aldehyde. Table 2 also shows the LC$_{50}$ results when CIDEX® OPA solution has been combined with an amino acid. In most cases, after one hour, the LC$_{50}$ of products generated from each of the reactions shown in Table 2 is greater than 500 mg/L which makes these wastes nonhazardous for toxicity as defined under California environmental law 22 CAL. CODE REGS., TIT. 22, §66696. The waste comprising aldehyde has been effectively neutralized.

TABLE 2

LC$_{50}$ Results Performed IN Accordance With 22 CAL. CODE REGS., TIT. 22, § 66696 For CIDEX ® OPA Solution Combined With Amino Acids

| Example | Molar Ratio OPA/ Amino Acids | Weight Ratio CIDEX ® OPA Solution/ Amino Acids | LC$_{50}$ Neutralization Time | |
|---|---|---|---|---|
| | | | LC$_{50}$ results, 1 hour after CIDEX ® OPA solution is first combined with Amino Acids | LC$_{50}$ results, 2 days after CIDEX ® OPA solution is first combined with Amino Acids |
| 1 | OPA/ glycine = 1:2 | 200 g/1.2 g of glycine | >1000 mg/L (See comment 1) | >1000 mg/L– 2000 mg/L |
| 2 | OPA/ arginine = 1:1 | 200 g/1.4 g of arginine | 500 mg/L– 1000 mg/L | >2000 mg/L |
| 3 | OPA/ lysine = 1:1 | 200 g/1.46 g of lysine | 100 mg/L– 500 mg/L | >2000 mg/L |
| 4 | OPA/ϵ- amino-n- caproic acid = 1:2 | 200 g/2.1 g of ϵ-amino- n-caproic acid | 1000 mg/L– 2000 mg/L | >2000 mg/L |

Comment 1: This data was determined based upon 22 CAL. CODE REGS., TIT. 22, § 66696, 96 hours bioassay. All other data was determined based upon 22 CAL. CODE REGS., TIT. 22, § 66696, 48 hour range bioassay.

In Example 1, CIDEX® OPA solution was neutralized with glycine at the molar ratio of 1:2 of OPA to glycine for one hour. The LC$_{50}$ for the neutralization product is >1000 mg/L, making the product nonhazardous under 22 CAL. CODE REGS., TIT. 22, §66696.

In Example 2, CIDEX® OPA solution was neutralized with arginine at a molar ratio of 1:1 of OPA to arginine for one hour. The LC$_{50}$ for the neutralization product is >500 mg/L, making the product nonhazardous under 22 CAL. CODE REGS., TIT. 22, §66696.

In Example 3, CIDEX® OPA solution was neutralized with lysine at the molar ratio of 1:1 of OPA to lysine for two (2) days. The LC$_{50}$ for the neutralization product is >2000 mg/L, making the product nonhazardous under 22 CAL. CODE REGS., TIT. 22, §66696.

In Example 4, CIDEX® OPA solution was neutralized with ϵ-amino-n-caproic acid for one hour. The LC$_{50}$ for the neutralization product is >1000 mg/L, which is nonhazardous under 22 CAL. CODE REGS., TIT. 22, §66696. The molar ratio used is 1:2 of OPA to ϵ-amino-n-caproic acid. The above examples demonstrate that the amino acids used with the aldehyde (e.g., OPA) effectively neutralize the aldehyde to acceptable levels in accordance with the Califormia hazardous waste rule. As shown above, glycine, lysine, arginine, and ϵ-amino-n-caproic acid are particularly useful at neutralizing aldehydes, but other amino acids are also effective. Glycine, one example of the neutralizer, is preferred as a 1D neutralizer for CIDEX® OPA Solution. A minimum of 25 g of glycine (free base) neutralizer and one hour neutralization time should be used to neutralize one gallon of CIDEX® OPA Solution. It should be noted that the invention described herein is not limited to amino acids in a free base form; rather, the amino acid may be in any physical form.

Table 3 shows the color change and the peak retention time (RT) change observed in a High Performance Liquid Chromatogram (HPLC) analysis after the CIDEX® OPA Solution was combined with amino acids. Colored products from the reaction product may act as an indicator of the effectiveness of the neutralizer. Darker colors such as black, orange, brown, or dark yellow typically indicate that the aldehyde has been neutralized to the levels established as nonhazardous for the current California regulations. But, sometimes such color appearance has the perception that the resulting solution is hazardous even though the solution has been neutralized.

Additionally, as shown in Table 3, the color of the mixture of OPA and the particular amino acid illustrates that neutralization of aldehydes occurs almost immediately when the amino acids are combined with aldehydes. The peak retention time in Table 3 shows the time when the molecule is beginning to change. The peak retention time for OPA is at approximately 1.812 minutes. As shown in Table 3, the OPA peak disappeared while some new peaks appeared after the two components were combined, indicating the OPA was reacting with the amino acids and the reaction products were formed. For example, after OPA is combined with glycine for fifteen minutes, the peak retention times are shown at 0.680 and 0.913 minutes which are different from the peak retention time of OPA that has a peak retention time of 1.812 minutes. These differences of peak retention times in glycine and OPA mixture compared to OPA without an amino acid show that the amino acid is reacting with the OPA. When the peak retention time is no longer significantly changing, the reaction is complete.

TABLE 3

Color Changes and Peak Retention Time (RT) of CIDEX ® OPA Solution Reaction with Amino Acids

| | OPA | Example 1 OPA/ glycine = 1:2 | | Example 2 OPA/ arginine = 1:1 | | Example 3 OPA/lysine = 1:1 | | Example 4 OPA/g-amino-n-caproic = 1:2 | |
|---|---|---|---|---|---|---|---|---|---|
| Neutralization Time | Peak RT (min) | Color | Peak RT (min) | Color | Peak RT (min) | Color | Peak RT (min) | Color | Peak RT (min) |
| Upon combining components | 1.812 | Red | 0.693 | Pink to Orange | 1.053 1.203 1.703 1.937 | Light Yellow | 0.9611 1.047 | Light Yellow Orange | 0.730 1.097 1.797 |
| | | Yellow | 1.010 1.677 | | | | | | |

TABLE 3-continued

Color Changes and Peak Retention Time (RT) of CIDEX ® OPA Solution Reaction with Amino Acids

| Neutralization Time | OPA Peak RT (min) | Example 1 OPA/glycine = 1:2 Color | Peak RT (min) | Example 2 OPA/arginine = 1:1 Color | Peak RT (min) | Example 3 OPA/lysine = 1:1 Color | Peak RT (min) | Example 4 OPA/g-amino-n-caproic = 1:2 Color | Peak RT (min) |
|---|---|---|---|---|---|---|---|---|---|
| 15 min | | Yellow Black | 0 680 0.913 | Orange | 1.013 | Yellow | 0.943 1.110 | Dark precipitate (ppt) | 0.727 0.942 |
| 30 min. | | Dark Brown | 0.685 0 918 | Orange | 1.023 | Dark Yellow | 0.923 | Dark ppt | 0.725 0.942 |
| 45 min. | | Dark Brown | 0.608 | Orange | 1 017 | Dark Yellow | 0.918 | Dark ppt | 0950 |
| 60 min. | | Black | 0.603 | Orange Brown | 1.027 | Dark Yellow | 0.913 | Dark ppt | 0.963 |

Moreover, agitating or stirring the solution increases the rates of neutralization of the aldehydes.

Table 4 shows various molar ratios of amino acids used to neutralize OPA wherein the OPA solution used contains ~0.55% OPA. In general, measurable neutralization begins after thirty minutes without physically stirring the solution. After one hour, most of the waste containing OPA has been neutralized in accordance with 22 CAL. CODE REGS., TIT. 22, §66696. Neutralization occurs at a faster rate if a higher concentration of amino acids is used and/or the solution is agitated.

TABLE 4

Neutralization Summary of Cidex ® OPA Solution with Amino Acids ($LC_{50}$ with Fathead Minnow)

| OPA/Amino Acids Molar Ratio | Time | | | | |
|---|---|---|---|---|---|
| | 5 min. | 15 min. | 30 min. | 1 hour | 2 days |
| OPA/L-Arginine, ($C_6H_{14}N_4O_2$) = 4:1 | <100 mg/L | <100 mg/L | <100 mg/L | Not available | Not available |
| OPA/L-Arginine, ($C_6H_{14}N_4O_2$) = 1:1 | Not available | Not available | Not available | 500 mg/L–1000 mg/L | >2000 mg/L |
| OPA/ε-Amino-n-Caprioc Acid, ($C_6H_{13}NO_2$) = 1:1 | <100 mg/L | <100 mg/L | 100–500 mg/L | Not available | Not available |
| OPA/ε-Amino-n-Caprioc Acid, ($C_6H_{13}NO_2$) = 1:2 | Not available | Not available | Not available | 1000 mg/L–2000 mg/L | >2000 mg/L |
| OPA/Glycine ($C_2H_5NO_2$) = 1.2 | Not available | Not available | Not available | >1000 mg/L | 1000 mg/L–2000 mg/L |
| OPA/Glycine ($C_2H_5NO_2$) = 1:4 | <100 mg/L | <100 mg/L | 100–500 mg/L | Not available | Not available |
| OPA/L-Lysine (Acetic Acid) ($C_6H_{14}N_2O_2 \cdot C_2H_4O_2$) = 1:1 | Not available | Not available | Not available | 100 mg/L–5000 mg/L | >2000 mg/L |
| OPA/L-Lysine (Acetic Acid) ($C_6H_{14}N_2O_2 \cdot C_2H_4O_2$) = 1:2 | <100 mg/L | ~100 mg/L | 100–500 mg/L | Not available | Not available |

As shown in Table 5, glycine is an effective neutralizer for glutaraldehyde solution. Combining 0.4 mole of glycine with 1 mole of glutaraldehyde for 30 minutes can provide a nonhazardous product as shown by an $LC_{50}$ result that is greater than the regulatory level of 500 mg/L. In this study, approximately 2.4% by weight of glutaraldehyde in buffered water solution was used.

TABLE 5

Fathead Minnow Test Results For Glutaraldehyde Solutions Neutralized With Glycine

| Glutaraldehyde/ Glycine Molar Ratio | 2.4% Glutaraldehyde Solution (g) | Glycine (g) | % Glycine in solution | Time | LC$_{50}$ (mg/L) |
|---|---|---|---|---|---|
| Glutaraldehyde/ Glycine = 1:0.4 | 200 | 1.4 | 0.7 | 30 minute | >2000 |
| Glutaraldehyde/ Glycine = 1:0.4 | 200 | 1.4 | 0.7 | 1 hour | >2000 |
| Glutaraldehyde/ Glycine = 1:0.77 | 200 | 2.8 | 1.4 | 30 minutes | >2000 |
| Glutaraldehyde/ Glycine = 1:0.77 | 200 | 2.8 | 1.4 | 1 hour | >2000 |
| Glutaraldehyde/ Glycine = 1:1.5 | 200 | 5.6 | 2.7 | 30 minutes | >2000 |
| Glutaraldehyde/ Glycine = 1:15 | 200 | 5.6 | 2.7 | 1 hour | >2000 |

Table 6 shows that glycine may neutralize formaldehyde in accordance with environmental regulations such as 22 CAL. CODE REGS., TIT. 22, §66696. In this study, approximately 2.5% by weight of formaldehyde in water was used.

TABLE 6

LC$_{50}$ Results Performed In Accordance With 22 CAL. CODE REGS., TIT. 22, § 66696 For Formaldehyde With Glycine

| Formaldehyde/ Glycine Molar Ratio | Formaldehyde solution (g) | Glycine (g) | % Glycine in mixed solution | Mixing Time | LC$_{50}$ (mg/L) |
|---|---|---|---|---|---|
| Formaldehyde Glycine Molar Ratio = 1:1 | 180 | 11.25 | 5.9 | 30 minutes | >500–1000 |
| Formaldehyde/ Glycine Molar Ratio = 1:1 | 180 | 11.25 | 5.9 | 1 hour | >500–1000 |
| Formaldehyde/ Glycine Molar Ratio = 1:4 | 180 | 45 | 24 | 30 minutes | >500–1000 |
| Formaldehyde/ Glycine Molar Ratio = 1:4 | 180 | 45 | 24 | 1 hour | >500–1000 |

Based upon the results shown in Table 6, glycine is capable of neutralizing formaldehyde to a level in which the waste product is considered nonhazardous.

While the discovery of forming neutralized aldehydes for lessening the toxic effects of disposing of aldehyde treated wastes was a major advance, the possibility of the neutralized aldehydes in reforming aldehydes under acidic conditions posed a problem in effectively maintaining nonhazardous waste because of the toxic effects of unneutralized aldehyde. The reversible reaction is depicted below for treatment of glutaraldehyde (1) and o-phthaladehyde (4) with the amino acid, glycine (2) to the neutralized products, (3) and (5), respectfully:

Reversible Schiff's Bases formation between Aldehydes and Glycine

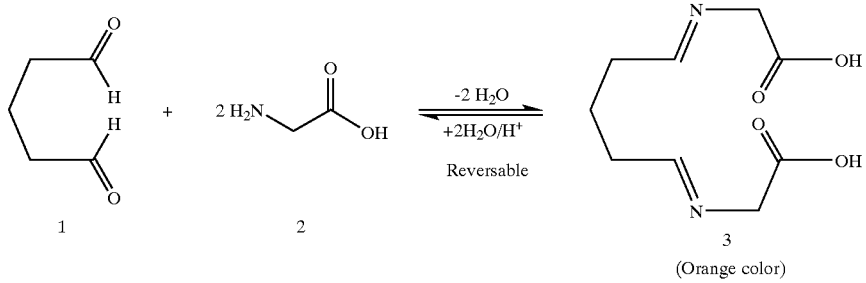

3 (Orange color)

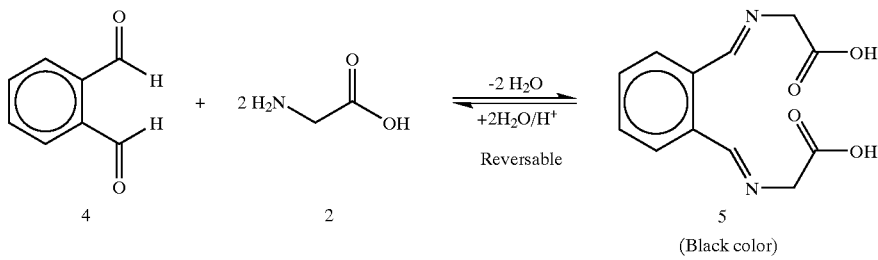

5 (Black color)

It has now been discovered that the treatment of the neutralized products with a reducing agent to form amino acids do not revert back to unneutralized aldehyde. This reaction is depicted below for saturated moieties (6) and (7) as for the reduction of Schiff's bases (3) and (5) treated with the reducing agent NaBH$_4$:

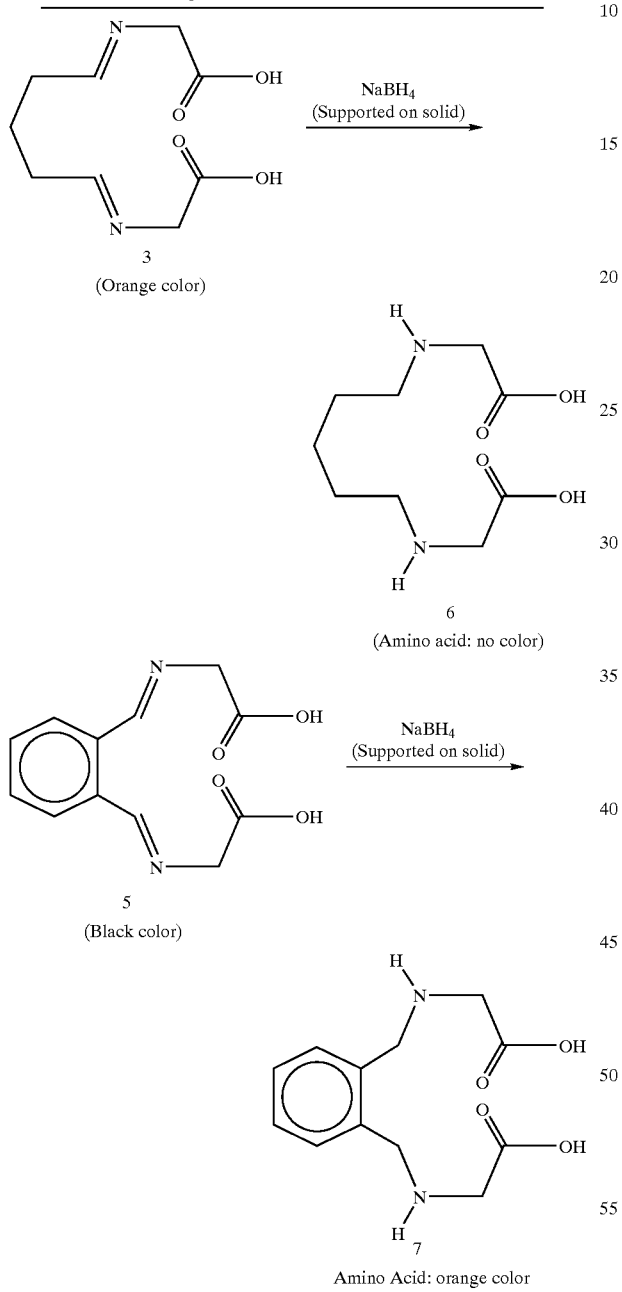

Being simple amino acids compounds (6) and (7) would be expected to be biodegradable and thus have significant benefit for the environment. This appears apparent by examination of the resemblance of the structures (6) and (7) with the natural essential amino acid proline, (8). The corresponding resemblance is depicted with bold-faced highlighting of compounds (6) and (7) shown below:

The Resemblance of Natural Amino Acid 8 with Amino Acid 6 and 7

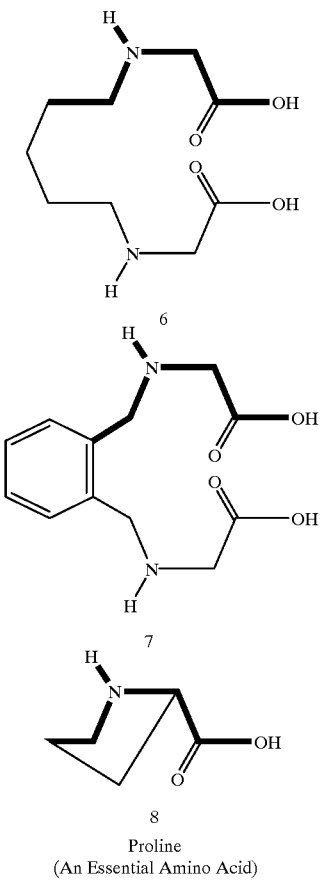

In contrast, Schiff's base (3) and (5) do not have the above characteristics and are likely very different compounds. One skilled in the art would suspect Schiff's bases to be harder to degrade in nature than the corresponding amino acids.

For example, a piece of animal skin could decay in a few days in the wild while men's belts, made from animal skin too, could take many years. This is because the belt (leather) has undergone a tanning process. Tanning processes often employ the glutaraldehyde derivatives, such as depicted as structures (9) and (10) below to cross-link proteins (Ref. a. Fein, M. L. and Filachione, E. M., "Tanning studies with aldehydes", *J. Am. Leather Chem. Assoc.,* 52, 17, 1957; b. Weligsberger, L. and Sadlier, C., "New developments in tanning with aldehydes", *J. Am. Leather Chem. Assoc.,* 52, 2, 1957; c. Hopwood, D., "Comparison of crosslinking abilities of glutaraldehyde, formaldehyde, and α-hydroxyadipaldehyde with bovine serum albumin and casein", *Histochemie,* 17, 151, 1969). It is well known that OPA has very similar protein cross-liking properties.

The Tanning Agents (Protein Cross-linkers)

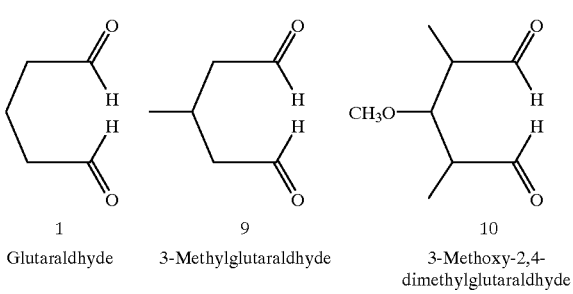

The conditions for Schiff's base reduction is easy and convenient. Normally, it involves the mixing of the reducing agent, such as NaBH4, and the imine, such as neutralized aldehyde, in a protonic solvent, such as water, ethanol, or methanol at room temperature.

Formation of the reduced neutralized aldehyde may be accomplished in any manner that results in a reduced neutralized aldehyde. Neutralization and reduction of aldehyde with amino acid and reducing agent can be conducted by mixing all three in a container, or reacting aldehyde with amino acid first, and then reacting the neutralized product with the reducing agent to reduce the neutralized product.

FIGS. 2a and 2b depict schematic mixing tanks containing aldehyde showing that amino acid and reducing agent (whether pre-mixed or separately) are added to the aldehyde (FIG. 2a) or the amino acid is added before the reducing agent (FIG. 2b).

In other embodiments, the reactions can be conducted by passing the aldehyde solution through a filter or cartridge containing amino acid and reducing agent with or without a solid support. The amino acid and the reducing agent can be coated onto a solid material. They can also be mixed or impregnated in the solid support. The amino acid and the reducing agent can be sandwiched between layers of glass wool with or without the solid support.

FIGS. 3a, 3b, and 3c depict schematics of filter or cartridge embodiments of the invention. FIG. 3a depicts treatment of an aldehyde waste. As shown, the aldehyde waste is discarded into a funnel, which directs the waste down a pipe or tube leading to a filter or cartridge. The filter or cartridge is detachable from the funnel. The filter/cartridge contains the neutralizing amino acid and the reducing agent. After contacting the amino acid and the reducing agent, the neutralized and reduced aldehyde is discharged.

The filter/cartridge may contain the amino acid and reducing agent in one or two zones. FIG. 3b depicts the one zone embodiment wherein the amino acid and the reducing agents are intimately mixed. FIG. 3c depicts a two-zone filter/cartridge wherein the first zone contains the neutralizing amino acid and the second zone contains the reducing agent.

A preferred method is first to contact the aldehyde with the neutralizer and then the reducing agent as shown below:

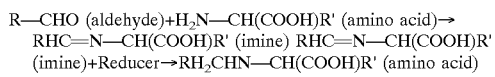

R—CHO (aldehyde)+H$_2$N—CH(COOH)R' (amino acid)→
RHC=N—CH(COOH)R' (imine) RHC=N—CH(COOH)R'
(imine)+Reducer→RH$_2$CHN—CH(COOH)R' (amino acid)

The imine can be reduced by many reducing agents, such as LiAlH$_4$ (Lithium aluminum hydride), NaBH$_4$ (Sodium borohydride), NaCNBH$_3$ (Sodium cyanoborohydride), Na—EtOH (Metal sodium in ethyl alcohol), and H$_2$/catalyst (Hydrogen with a catalyst). A preferred reducing agent is NaBH$_4$.

Figure 4:
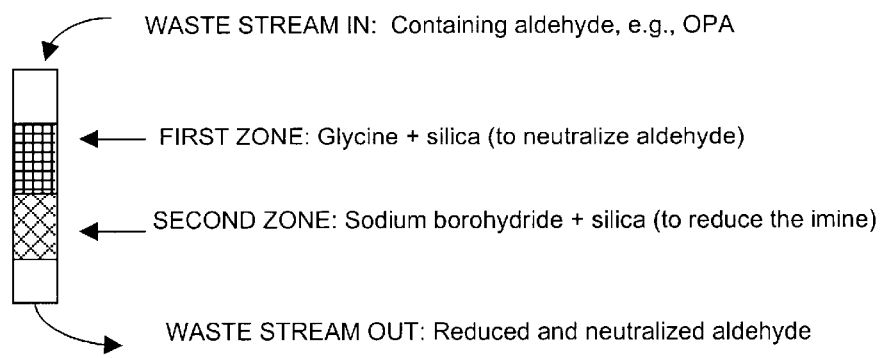
FIG. 4 shows a preferred embodiment of a device of this invention.

One preferred way to accomplish the reduced neutralization of aldehyde is to use a device as shown in FIG. 4. Referring to FIG. 4, the waste stream containing aldehyde, in this case OPA, in introduced into the device depicted here as a cylinder. The entering OPA passes into a first zone, which neutralizes the OPA forming an imine. In this embodiment, the first zone is depicted to comprise the amino acid glycine supported on silica. After passing through the first zone, the neutralized OPA passes through a second zone, which reduces the neutralized OPA. In this case, the second zone comprises the reducing agent, NaBH$_4$ supported on silica. Upon exiting the device, the aldehyde is non-reversibly neutralized and thus should not revert back to the toxic aldehyde form.

Suitable amino acids and reducing agents include all of the ones previously described above.

Suitable support materials include any solid material capable of mixing with but not reacting with the amino acid or reducing agent. Such materials include salts, polymers and, more specifically silica, celite, sand, alumina, metal powders, carbon black, clay, pulps, zeolite, or starch. Preferred is silica.

The amino acids and reducing agents may be supported on the support materials in many ways. Most simply the amino acids and reducing agents are mixed together or separately with the support material in a wide variety of ratios. The amino acid or reducing agent may be coated or impregnated on the support by conventional means, again providing there is no reaction between the amino acid and reducing agent with the support.

The feasibility of the device depicted in FIG. 4 is demonstrated in the following examples

EXAMPLE 5

Figure 5:
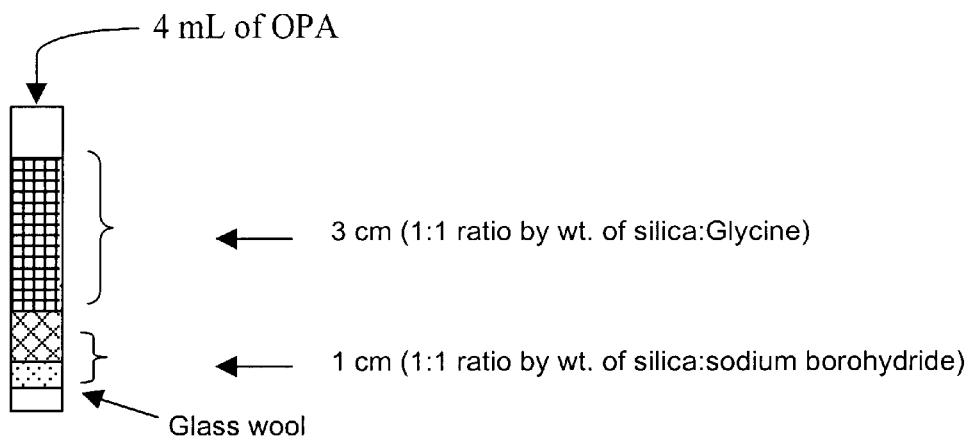
FIG. 5 depicts the experimental setup for Example 5.

In a plastic column (0.3×5 cm), as shown in FIG. 5, a small amount of glass wool is inserted near the bottom of the column to form a support. To the column was then added a 1:1 by weight mixture of some sodium borohydride and Aldrich silica. The sodium borohydride/silica was added in an amount to comprise 1 cm of the column. Then a mixture of 1:1 by weight mixture of some glycine and Aldrich silica was added in an amount to comprise 3 cm of the column. 4 ml of OPA was added from the top of the column and collected at the bottom of the column. The fluid exiting the column was a brown solution which did not turn green or dark green after standing even when more glycine was added. This concludes that Schiff's base was converted to the saturated species and that the neutralized aldehyde was reduced

EXAMPLE 6

Figure 6:
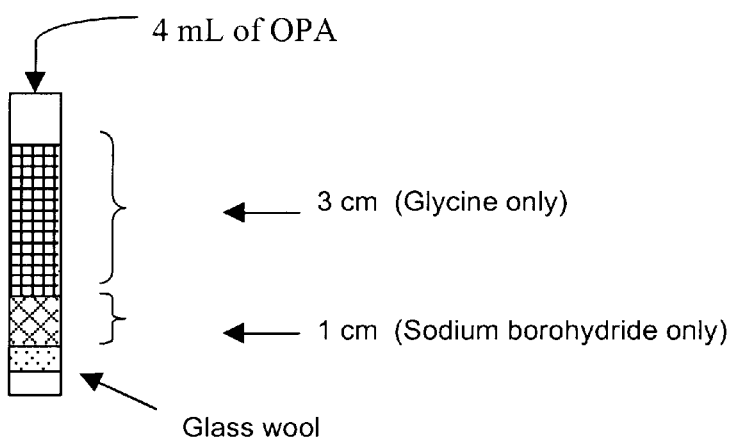
FIG. 6 depicts the experimental setup for Example 6.

In this example, the same procedure was followed as in Example 5 except that no silica was used. Sodium borohydride was placed in the column, as shown in FIG. 6, in an amount to form a height of 1 cm in the column. Glycine was then placed on top of the sodium borohydride in an amount to form a height of 3 cm in the column. When the 4-ml of OPA was added, identical results were obtained as in Example 5.

In the preceding detailed description, the invention is described with reference to specific embodiments thereof. It will, however, be evident that various modifications and changes may be made thereto without departing from the broader spirit and scope of the invention as set forth in the claims. The specification and drawings are, accordingly, to be regarded in an illustrative rather than a restrictive sense.

What is claimed is:

1. A method for forming a non reversible and nonhazardous product comprising the steps of:
    a) combining a neutralizer comprising an amino acid with an aldehyde to form a neutralized product; and
    b) reducing the neutralized product with a reducing agent to yield a non-hazardous waste which has a LC$_{50}$>500 mg/l.

2. The method of claim 1, wherein the amino acid is selected from an amino acid defined by the general formula RCH(NH$_2$)(COOH) wherein R is an apolar moiety.

3. The method of claim 1, wherein the amino acid is selected from an amino acid defined by the general formula RCH(NH$_2$)(COOH) wherein R is a polar moiety.

4. The method of claim 1, wherein the amino acid is selected from an amino acid defined by the general formula RCH(NH$_2$)(COOH) wherein R is a charged moiety.

5. The method of claim 1, wherein the amino acid is selected from the group consisting of peptides or polypeptides formed by any number of amino acids and proteins.

6. The method of claim 1, wherein the amino acid is selected from the group consisting of alanine, proline, amino-caproic acid, phenylalanine, tryptophan, methionine, glycine, serine, cytoseine, tyrosine, arginine, lysine, ε-amino-n-caproic acid, and glutamine or any combination thereof.

7. The method of claim 1, wherein the aldehyde comprises a dialdehyde.

8. The method of claim 7, wherein the aldehyde comprises a glutaraldehyde.

9. The method of claim 7, wherein the dialdehyde comprises ortho-phthalaldehyde.

10. The method of claim 1, wherein the molar amount of amino acid combined with aldehyde in the contained waste is at least in the range of 0.2:1 to 8:1 moles.

11. The method of claim 1, wherein the amount of amino acid combined with aldehyde in the contained waste is at least in the range of 1:1 to 4:1 moles.

12. The method of claim 7, wherein the amount of amino acid combined with dialdehyde in the contained waste is at least in the range of 0.2:1 to 8:1 moles.

13. The method of claim 7, wherein the amount of amino acid combined with dialdehyde in the contained waste is at least in the range of 1:1 to 4:1 moles.

14. The method of claim 1, wherein the aldehyde comprises formaldehyde.

15. The method of claim 1, wherein the aldehyde comprises a germicide.

16. The method of claim 1, wherein the reducing agent is selected from the group consisting of $LiAlH_4$, $NaBH_4$, $NaCNBH_3$, Na-Ethyl Alcohol, and hydrogen with a catalyst or any combination thereof.

17. The method of claim 1, further comprising sterilizing an article with an aldehyde wherein the aldehyde is selected from the group consisting of ortho-phthalaldehyde, formaldehyde and glutaraldehyde or any combination thereof.

18. A method comprising the steps of:
   (a) combining a neutralizer comprising an amino acid with an aldehyde, wherein the aldehyde is selected from the group consisting of ortho-phthalaldehyde, glutaraldehyde, formaldehyde and mixtures thereof, to form a neutralized aldehyde; and
   (b) combining the neutralized aldehyde with a reducing agent to form a reduced, neutralized aldehyde, wherein the reducing agent is selected from the group consisting of $LiAlH_4$, $NaBH_4$, $NaCNBH_3$, Na-Ethyl Alcohol, and hydrogen with a catalyst or any combination thereof to yield a non-hazardous waste which has a $LC_{50}>500$ mg/l.

19. The method of claim 18, wherein the amino acid is selected from the group consisting of alanine, proline, amino-caproic acid, phenylalanine, tryptophan, methionine, glycine, serine, cytoseine, tyrosine, arginine, lysine, and glutamine or any combination thereof.

20. The method of claim 19, where the amino acid is glycine.

21. The method of claim 1 or 18 wherein the neutralizing agent and reducing agent are combined at the same time, either separately or mixed together.

* * * * *